United States Patent [19]

Madsen et al.

[11] Patent Number: 5,378,722
[45] Date of Patent: Jan. 3, 1995

[54] NUTRITIONAL COMPOSITIONS FOR MANAGEMENT OF NITROGEN METABOLISM

[75] Inventors: David C. Madsen, Libertyville; David Mark, Oak Park, both of Ill.

[73] Assignee: Clintec Nutrition Co., Deerfield, Ill.

[21] Appl. No.: 161,917

[22] Filed: Dec. 3, 1993

[51] Int. Cl.$^6$ .............................................. A01N 43/38
[52] U.S. Cl. .................................................. 514/410
[58] Field of Search ............................ 514/410, 18, 19

[56] References Cited

U.S. PATENT DOCUMENTS 4,340,592  7/1982  Adibi ........................................ 514/19
5,034,377  7/1991  Adibi et al. ............................. 514/18

Primary Examiner—Arthur C. Prescott
Attorney, Agent, or Firm—Hill, Steadman & Simpson

[57] ABSTRACT

A nutritional composition is provided that is low ammoniagenic, scavenges ammonia well, and yet does not contribute to excess nitric oxide production. The nutritional composition includes an amino acid profile having less than 20 percent of the total amino acids as ammoniagenic amino acids. The nutritional composition also includes less than 0.2 percent of the total amino acids as arginine and at least 0.2 percent of the total amino acids as ornithine and/citrulline.

18 Claims, No Drawings

NUTRITIONAL COMPOSITIONS FOR MANAGEMENT OF NITROGEN METABOLISM

BACKGROUND OF THE INVENTION

The present invention relates to compositions and methods for providing nutrition. More specifically the present invention relates to compositions and methods for the nutritional management of nitrogen metabolism.

In the quest for sufficient food energy to meet caloric requirements, animals ingest more nitrogen, largely as amino acids, than they require. Accordingly, the excess nitrogen ingested must be excreted in some form. Through the action of a series of related enzymes called transaminasis, virtually all metabolic nitrogen can be transferred to α-ketoglutaric acid to form glutamic acid. Under the influence of glutamic dehydrogenase, glutamic acid may be oxidized by the coenzyme diphosphopyridine nucleotide (DPN) with the reformation of α-ketoglutaric acid plus ammonia.

Since the resulting ammonia produced from the oxidation of glutamic acid is toxic if it exceeds "normal" levels, the body systems of animals work to convert the ammonia into urea to maintain ammonia levels at acceptable levels. The liver is the major site where ammonia is detoxified, by the concurring interaction of both the urea cycle and the glutamine/glutamate cycle.

To accomplish the conversion of ammonia to urea, advantage is taken of the enzymically catalyzed metabolic sequence by which the amino acid arginine is synthesized from ornithine, a sequence common to almost all living forms. Arginase catalyzes the hydrolysis of arginine to urea plus ornithine, which is then available for recycling.

If the liver is compromised in its ability to detoxify ammonia, due to systemic overproduction, hepatic disease, disordered glutamine/glutamate metabolism, and acidosis, ammonia levels can increase to unacceptable levels. A common response to prevent excess ammonia in these states is to terminate all nitrogen-containing feeds. However, this is clinically unacceptable.

An alternate maneuver is to provide a nutritional source (especially the protein fraction) that produces minimal ammonia. This approach is the basis for a number of commercial products, that are designed to provide nutritional support to hepatic patients. With such products, the profile of amino acids is designed to minimize the content of those amino acids that are the most potent in terms of yielding free ammonia upon metabolism commonly known as "ammonotelic" amine acids. The ammonotelic amino acids (all in L-forms) are: glycine; threonine; serine; histidine; tryptophan; glutamine; and methionine. Limiting the production of ammonotelic amino acids minimizes the exogenous provision of a source of ammonia.

An adjunctive nutritional strategy to enhance the detoxification of ammonia is to provide generous amounts of arginine. Arginine is well known to be a major and effective "stimulator" of urea cycle function, and has been so used clinically.

Certain patients may have a relatively impaired ability to efficiently detoxify ammonia. These patients include those having: severe trauma and/or sepsis; renal disease; and hepatic disease. Providing diets that are low in ammonotelic amino acids but contain generous amounts of arginine may effectively manage "nitrogen waste" problems in such patients.

However, high levels of dietary arginine can be deleterious in certain clinical conditions. Arginine, in addition to its role in the urea cycle, creatinine and protein synthesis, is a precursor molecule for nitric oxide production. Inflammatory reactions to bacterial infection, severe trauma or burns trigger the release of "inflammatory mediators," such as leukotrienes, complement, and cytokines (e.g., interleukin-2, tumor necrosis factor). These inflammatory mediators in turn induce the release of nitric oxide.

Nitric oxide is a potent vasodilator and generator of free oxygen radicals. The result of nitric oxide action is unresponsive hypotension, oxidative tissue damage, multiple organ dysfunction syndrome and septic shock thus, arginine can worse the condition of such patients.

Therefore, a need exists for a nutritional composition that can be administered to patients with actual or potential increased ammonia levels and can provide nutritional support to the patient without generating excess nitric oxide in the patient.

SUMMARY OF THE INVENTION

The present invention provides a nutritional composition for use in managing patients who have a compromised ability to detoxify ammonia, yet in whom one should minimize stimulation of nitric oxide. The nutritional composition preferably includes an amino acid profile having less than 20% percent of the total amino acids as ammoniagenic amino acids. In addition, the nutritional composition includes less than 0.2 percent of the total amino acids as arginine and at least 0.2 percent of the total amino acids as ornithine and/or citrulline.

In an embodiment, the nutritional composition includes no arginine.

In an embodiment, the nutritional composition includes amino acids obtained from a protein source chosen from the group consisting of whole protein, protein hydrolysates, peptides, and free amino acids. In an alternative embodiment, the nutritional composition includes amino acids obtained from a mixture of such protein sources.

The present invention also provides a method for providing nutritional support to a patient in need of same. The method includes the step of administering a nutritional composition that includes an amino acid profile having less than 20 percent of the total amino acids as ammoniagenic amino acids, less than 0.2 percent of the total amino acids as arginine, and at least 0.2 percent of the total amino acids as ornithine and/or citrulline to such patient. The composition can be administered enterally, parenterally, or through the peritoneum.

Moreover, the present invention provides a method for providing nutrition to a hepatic patient in need of same without generating excess nitric oxide in the patient. The method includes administering to such patient a nutritional composition having an amino acid profile having reduced ammoniagenic amino acids, reduced arginine levels, and including ornithine and/or citrulline.

The present invention also provides a method for creating a nutritional composition for a hepatic patient that provides nutritional support without generating excess nitric oxide comprising the steps of reducing the level of ammoniagenic amino acids, reducing the arginine levels, and adding ornithine and/or citrulline.

An advantage of the present invention is that it provides a nutritional composition that effectively detoxifies ammonia in a patient, while at the same time minimizes stimulation of nitric oxide.

Another advantage of the present invention is that it not only provides compositions and methods for the nutritional management of nitrogen metabolism, it simultaneously provides a complete nutritional supplement.

Still further, an advantage of the present invention is that it provides an improved treatment program for patients having a relatively impaired ability to efficiently detoxify ammonia, such as those suffering from sever trauma and/or sepsis, renal disease and hepatic disease.

Moreover, an advantage of the present invention is to provide a method for creating nutritional products for hepatic patients.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides nutritional compositions for managing patients with a compromised ability to detoxify ammonia. The composition, however, does not increase the risk of excessive production of nitric oxide. The present invention also provides a method for providing nutritional support to a patient in need of same without generating excess nitric oxide in the patient.

The nutritional composition of the present invention is low ammoniagenic, scavenges ammonia well, and yet does not contribute to excess nitric oxide production. Pursuant to the present invention, the nutritional composition includes an amino acid profile having less than 20 percent of the total amino acids as ammoniagenic amino acids. In addition, the nutritional composition includes less than 0.2 percent of the total amino acids as arginine and at least 0.2 percent of the total amino acids as ornithine and/or citrulline.

The inventors have found that by utilizing the dietary amino acids ornithine and/or citrulline in the composition of the present invention, a composition is provided that maximizes the patient's ability to handle ammonia without the production of excess nitric oxide. The nutritional compositions of the present invention provide a diet low in ammoniagenic amino acids, while eliminating or reducing arginine.

As noted above, ornithine and/or citrulline are included in the compositions of the present invention. Although ornithine or citrulline are not essential amino acids, along with arginine, they are the other major amino acids in the urea cycle. As a result, ornithine and citrulline act as effective substitutes for arginine and are effective simulators of urea cycle function.

In certain pathological circumstances (e.g., inborn errors of the urea cycle, liver failure, trauma, protein malnutrition), ornithine can become limiting for urea cycle function. Ornithine and arginine are relatively equivalent in their effectiveness in stimulating the urea cycle. Citrulline is nearly as effective as arginine. Ornithine and citrulline can thereby protect against ammonia toxicity in humans.

Pursuant to the present invention, a nutritional composition is provided that contains effective amounts of ornithine and/or citrulline, while reducing or eliminating arginine. The proper amount of arginine present in the nutritional composition depends on the extent of the patient's impaired ability to efficiently detoxify ammonia. Naturally, the patient's impaired ability is directly related to the type of disease being treated.

Since the present invention provides effective substitutes for arginine, lower amounts of arginine are needed to effectively manage ammonia derived from deamination of amino acids. Currently, arginine makes up approximately 4 to about 6 percent of most dietary proteins and supplies approximately 0.8 to about 0.9 percent of total calories in a typical U.S. diet. Most enteral supplements fall slightly below this range. Casein- and whey-based products have arginine as approximately 2.5 to about 4 percent of protein and supply approximately 0.4 to about 0.6 percent of total calories as arginine. Products which have a high protein concentration and those which are soy-based have more arginine. Some arginine enriched products contain approximately 2 to about 6 percent of total calories as arginine.

Most parental amino acid formulations are above the normal intake range, containing approximately 9 to about 11 percent of their protein as arginine. As a result, these parental amino acid formulations deliver approximately 1.5 to about 2.5 percent of total calories as arginine.

In an embodiment, the nutritional composition of the present invention contains less than 0.2% of the total calories as arginine. In a preferred embodiment, the nutritional composition contains less than 0.1% of the total calories as arginine. In an embodiment, the composition does not include arginine.

The nutritional composition of the present invention not only provides effective components for nutritional management of nitrogen metabolism, it also provides a complete nutritional supplement. To this end, the nutritional composition includes a protein source that acts as an effective nutritional supplement. The nutritional composition includes amino acids obtained from a protein source chosen from a group consisting of whole protein, protein hydrolysates, peptides and free amino acids. Alternatively, the amino acids may be obtained from a mixture of such protein sources.

Additionally, the present invention provides methods for creating compositions for hepatic patients. The method includes the steps of: reducing the ammoniagenie amino acids; reducing the amount of arginine; and substituting therefore ornithine and/or citrulline.

By way of example, and not limitation, examples of suitable compositions of the present invention will be given.

EXAMPLE 1

A suitable composition is one comprising protein in addition to other components such as lipids, carbohydrates, etc. The protein source is provided exclusively by free amino acids. Such a composition may consist of the following amino acids in the stated proportions:

| AMINO ACID (L-form) | MOLE PERCENT RANGE ABOUT FROM: |
|---|---|
| Leucine | 20.0 to 8.5 |
| Isoleucine | 6.2 to 16.4 |
| Valine | 9.0 to 15.0 |
| Phenylalanine | 0.6 to 3.8 |
| Methionine | 5.2 to 1.1 |
| Lysine (free base) | 4.5 to 6.0 |
| Threonine | 6.0 to 2.2 |
| Tryptophan | 0.5 to 1.5 |

-continued

| AMINO ACID (L-form) | MOLE PERCENT RANGE ABOUT FROM: |
|---|---|
| Histidine | 6.8 to 2.5 |
| Arginine | 0 to 0.05 |
| Glycine | 0 to 6.9 |
| Serine | 0 to 4.5 |
| Proline | 4.9 to 8.3 |
| Alanine | 14.5 to 5.3 |
| Tyrosine | 0.2 to 0.8 |
| Ornithine | 3.5 to 8.7 |
| Citrulline | 0 to 8.7 |

EXAMPLE 2

Another suitable composition includes as a protein source hydrolyzed whey protein and free amino acids. For example, the following general formula may be used pursuant to the present invention: 11% of total calories as protein (23% hydrolyzed whey protein, 77% free amino acids); arginine (from all sources) as 0.0 to 0.2% of total calories; and ornithine and/or citrulline as 0.2 to 0.8% of total calories.

In formulations, such as the above example, that are not comprised exclusively of free amino acids, a rigorous definition of a suitable amino acid profile is difficult. These formulations include those including whole protein, protein hydrolyzates, other sources of peptides, or mixtures of all three of these sources. In these cases, employing a protein source (intact or hydrolyzed) that is very low in arginine, such as whey protein, is desirable. Such a protein source can then be supplemented with other amino acids, such as ornithine and/or citrulline, or other amino acids as needed to adjust the profile to a desired range.

The present invention also provides a method for providing nutritional support to a patient in need of same. Examples of patients having a relatively impaired ability to efficiently detoxify ammonia and thus in need of nutritional support include, among others, those suffering from: severe trauma and/or sepsis; renal disease; and hepatic disease. The method includes the step of administering a composition having less than 20 percent of the total amino acid content as ammoniagenic amino acids. In addition, the composition contains less than 0.2 percent of the total amino acid content as arginine and at least 0.2 percent of the total amino acid content as ornithine and/or citrulline.

The nutritional compositions of the present invention can be administered either enterally, parenterally or through the peritoneum of the patient.

It should be understood that various changes and modifications to the presently preferred embodiments described herein will be apparent to those skilled in the art. Such changes and modifications can remain without departing from the spirit and scope of the present invention and without diminishing its intended advantages. It is therefore intended that such changes and modifications be covered by the appended claims.

We claim:

1. A nutritional composition comprising:
   An amino acid profile having less than 20% of the total amino acids as ammoniagenic acids;
   including less than 0.2% of the total amino acids as arginine; and
   at least 0.2% of the total amino acids as at least one of an amino acid selected from the group consisting of: ornithine and citrulline.

2. The nutritional composition of claim 1 wherein the composition includes no arginine.

3. The nutritional composition of claim 1 wherein the composition has the following amino acids profile in mole percent:
   Leucine (20.0 to 8.5);
   Isoleucine (6.2 to 16.4);
   Valine (9.0 to 15.0);
   Phenylalanine (0.6 to 3.8);
   Methionine (5.2 to 1.1);
   Lysine (free base) (4.5 to 6.0);
   Threonine (6.0 to 2.2);
   Tryptophan (0.5 to 1.5);
   Histidine (6.8 to 2.5);
   Arginine (0 to 0.05);
   Glycine (0 to 6.9);
   Serine (0 to 4.5);
   Proline (4.9 to 8.3);
   Alanine (14.5 to 5.3);
   Tyrosine (0.2 to 0.8);
   Ornithine ( 3.5 to 8.7 ); and
   Citrulline (0 to 8.7).

4. The nutritional composition of claim 1 wherein the composition includes amino acids obtained from a protein source selected from the group consisting of: whole protein; protein hydrolysates; peptides; or free amino acids.

5. A method for providing nutritional support to a patient in need of same comprising the steps of administering a composition having less than 20% of the total amino acid content as ammoniagenic amino acids, less than 0.2 % of the total amino acid content as arginine; and at least 0.2 % of the total amino acid content as at least one amino acid selected from the group consisting of: ornithine and citrulline.

6. The method of claim 5 wherein the composition is administered enterally.

7. The method of claim 5 wherein the composition is administered parenterally.

8. The method of claim 5 wherein the composition is administered through the peritoneum.

9. The method of claim 5 wherein the patient suffers from hepatic disease.

10. The method of claim 5 wherein the nutritional composition includes no arginine.

11. The method of claim 5 wherein the nutritional composition includes an amino acid profile in mole percent as follows:
    Leucine (20.0 to 8.5);
    Isoleucine (6.2 to 16.4);
    Valine (9.0 to 15.0);
    Phenylalanine (0.6 to 3.8);
    Methionine (5.2 to 1.1);
    Lysine (free base) (4.5 to 6.0);
    Threonine (6.0 to 2.2);
    Tryptophan (0.5 to 1.5);
    Histidine (6.8 to 2.5);
    Arginine (0 to 0.5);
    Glycine (0 to 6.9);
    Serine (0 to 4.5);
    Proline (4.9 to 8.3);
    Alanine (14.5 to 5.3);
    Tyrosine (0.2 to 0.8);
    Ornithine (3.5 to 8.7); and
    Citrulline (0 to 8.7).

12. A method for providing nutrition to a hepatic patient in need of same without generating excess nitric oxide in the patient comprising the steps of administering a composition having an amino acid profile in mole percent as follows:
- Leucine (20.0 to 8.5);
- Isoleucine (6.2 to 16.4);
- Valine (9.0 to 15.0);
- Phenylalanine (0.6 to 3.8);
- Methionine (5.2 to 1.1);
- Lysine (free base) (4.5 to 6.0);
- Threonine (6.0 to 2.2);
- Tryptophan (0.5 to 1.5);
- Histidine (6.8 to 2.5);
- Arginine (0 to 0.05);
- Glycine (0 to 6.9);
- Serine (0 to 4.5);
- Proline (4.9 to 8.3);
- Alanine (14.5 to 5.3);
- Tyrosine (0.2 to 0.8);
- Ornithine (3.5 to 8.7); and
- Citrulline (0 to 8.7).

13. The method of claim 12 wherein the nutritional composition includes no arginine.

14. The method of claim 12 wherein the composition is administered enterally.

15. The method of claim 12 wherein the composition is administered parenterally.

16. The method of claim 12 wherein the composition is administered through the peritoneum.

17. A method for creating a nutritional product for a hepatic patient comprising the steps of: reducing the ammoniagenic amino acid content of a typical nutritional composition and replacing at least a portion of the arginine content with at least one amino acid selected from the group consisting of ornithine and citrulline.

18. The method of claim 17 comprising the step of providing an amino acid profile in mole percent as follows:
- Leucine (20.0 to 8.5);
- Isoleucine (6.2 to 16.4);
- Valine (9.0 to 15.0);
- Phenylalanine (0.6 to 3.8);
- Methionine (5.2 to 1.1);
- Lysine (free base) (4.5 to 6.0);
- Threonine (6.0 to 2.2);
- Tryptophan (0.5 to 1.5);
- Histidine (6.8 to 2.5);
- Arginine (0 to 0.05);
- Glycine (0 to 6.9);
- Serine (0 to 4.5);
- Proline (4.9 to 8.3);
- Alanine (14.5 to 5.3);
- Tyrosine (0.2 to 0.8);
- Ornithine (3.5 to 8.7); and
- Citrulline (0 to 8.7).

* * * * *